(12) United States Patent
Woodruff

(10) Patent No.: US 11,103,360 B2
(45) Date of Patent: Aug. 31, 2021

(54) SPINAL FUSION CAGE AND METHOD OF OPERATION

(71) Applicant: Robert Woodruff, Rapid City, SD (US)

(72) Inventor: Robert Woodruff, Rapid City, SD (US)

( * ) Notice: Subject to any disclaimer, the term of this patent is extended or adjusted under 35 U.S.C. 154(b) by 0 days.

(21) Appl. No.: 16/822,433

(22) Filed: Mar. 18, 2020

(65) Prior Publication Data

US 2020/0297510 A1     Sep. 24, 2020

Related U.S. Application Data

(60) Provisional application No. 62/820,576, filed on Mar. 19, 2019.

(51) Int. Cl.
*A61F 2/44*     (2006.01)

(52) U.S. Cl.
CPC .... *A61F 2/4455* (2013.01); *A61F 2220/0016* (2013.01); *A61F 2220/0041* (2013.01); *A61F 2230/0013* (2013.01); *A61F 2310/00359* (2013.01)

(58) Field of Classification Search
CPC .................. A61F 2/4455; A61F 2220/0016
See application file for complete search history.

(56) References Cited

U.S. PATENT DOCUMENTS

| | | |
|---|---|---|
| 4,904,261 A | 2/1990 | Dove et al. |
| 5,397,364 A | 3/1995 | Kozak et al. |
| 6,342,074 B1 | 1/2002 | Simpson |
| 7,112,222 B2 | 9/2006 | Fraser et al. |
| 8,343,219 B2 | 1/2013 | Allain et al. |
| 8,523,945 B1 | 9/2013 | Wensel |
| 8,617,245 B2 | 12/2013 | Brett |
| 8,932,359 B2 | 1/2015 | Brett |
| 8,945,221 B2 | 2/2015 | Barrett |
| 9,101,489 B2 | 8/2015 | Protopsaltis et al. |
| 9,463,091 B2 | 10/2016 | Brett |
| 9,713,535 B2 | 7/2017 | Davis et al. |
| 9,737,412 B2 | 8/2017 | Brett |
| 9,750,616 B2 | 9/2017 | Blain et al. |
| 9,795,485 B2 | 10/2017 | Allain et al. |
| 9,872,780 B2 | 1/2018 | Reed et al. |
| 10,166,115 B2 | 1/2019 | Kana et al. |

(Continued)

FOREIGN PATENT DOCUMENTS

WO    WO-2014184367 A1 * 11/2014 ........... A61F 2/4455

OTHER PUBLICATIONS

Zimmer Biomet Spine, Inc., ROI-A ALIF Cage System with VerteBRIDGE Fixation Brochure, 2016.

(Continued)

*Primary Examiner* — Brian A Dukert
(74) *Attorney, Agent, or Firm* — David R. Heckadon; Gordon Rees Scully Mansukhani LLP

(57) ABSTRACT

A spinal fusion cage, having a C-shaped posterior body with a plurality of insertable shims passing therethrough and into a vertebral body above or below the C-shaped posterior body; an anterior plate that is attachable to the opposite ends of the C-shaped posterior body; and a plurality of screws passing through the anterior plate and extending into a vertebral body above or below the anterior plate.

11 Claims, 16 Drawing Sheets

(56) References Cited

U.S. PATENT DOCUMENTS

| | | |
|---|---|---|
| 10,751,187 B2 | 8/2020 | Allain et al. |
| 2005/0177236 A1 | 8/2005 | Mathieu et al. |
| 2008/0306596 A1 | 12/2008 | Jones et al. |
| 2010/0057206 A1 | 3/2010 | Duffield et al. |
| 2010/0106249 A1 | 4/2010 | Tyber et al. |
| 2011/0153020 A1 | 6/2011 | Abdelgany et al. |
| 2012/0277873 A1 | 11/2012 | Kana et al. |
| 2013/0079879 A1 | 3/2013 | Suh |
| 2013/0190874 A1 | 7/2013 | Glazer |
| 2013/0261747 A1 | 10/2013 | Geisert |
| 2017/0325968 A1 | 11/2017 | Blain et al. |
| 2018/0104067 A1 | 4/2018 | Skolnick et al. |
| 2018/0360614 A1 | 12/2018 | Wu et al. |
| 2018/0368992 A1 | 12/2018 | Zink et al. |
| 2019/0000637 A1 | 1/2019 | Gilbride et al. |

OTHER PUBLICATIONS

Zimmer Biomet, Roi-C Cervical Cage Surgical Technique Guide, 2018, 32 pages.

* cited by examiner

SPINAL FUSION CAGE AND METHOD OF OPERATION

RELATED APPLICATION

The present application claims priority to U.S. Provisional Patent Application 62/820,576, of same title, filed Mar. 19, 2019, the entire disclosure of which is incorporated herein by reference in its entirety.

TECHNICAL FIELD

The present invention relates to spinal fusion cages.

BACKGROUND OF THE INVENTION

Description of Problem

Lumbar spinal fusion is a frequently performed procedure and can be done through several different approaches. The posterior approach to fusion is the most common but is associated with significant approach-related morbidity in many cases. Because of this, there is an interest in finding new ways to fuse the spine without disrupting the posterior anatomy. One of these methods is through a stand-alone anterior lumbar interbody fusion (ALIF) or lateral lumbar interbody fusion (LLIF, XLIF, OLIF). These approaches have the advantage of the ability to place a large cage in the interbody space where fusion is the most likely to occur. Fixation is typically done with screws placed through a plate either over the anterior or lateral aspect of the vertebral bodies or attached to the cage itself.

Unfortunately, although this fixation is convenient and easily accessible, it lacks in mechanical stability, especially in resisting flexion and rotation. Because of this, patients who undergo a stand-alone ALIF or lateral procedure usually have to wear a very restrictive brace for 6-8 weeks following the surgery. Limited compliance with the brace and post-operative restrictions can lead to suboptimal surgical outcomes.

Prior Art

Intervertebral cages come in many different forms. The most common designs are variations of either an oval or a figure-eight cage. These are hollow to provide an area to pack bone graft prior to inserting the cage into the disc space. These can be made of a variety of materials including PEEK, titanium, carbon fiber, and tantalum, among others. In addition, many incorporate a porous surface that allows for boney in-growth to assist in long-term stabilization of the fusion. Anterior fixation is achieved through plates placed separately from the cage, plates that integrate with the cage, and cages designed so that the fixation can be placed through the cage itself. Fixation can most commonly be achieved with screws or shims.

Nevertheless, the need still exists for a new approach to spinal fusion, preferably avoiding a posterior approach into the spinal column.

SUMMARY OF THE INVENTION

The present system provides a spinal fusion cage, comprising: (a) a C-shaped posterior body having opposite lateral ends with an open center region for receiving bone graft material therein; (b) a plurality of shim tracts passing through the C-shaped posterior body; (c) a plurality of shims, each shim passing through one of the shim tracts and extending out from the C-shaped posterior body and into a vertebral body above or below the C-shaped posterior body to provide anchoring in the posterior region of the fusion cage; (d) an anterior plate, the anterior plate being attachable to the opposite ends of the C-shaped posterior body; and (e) a plurality of screws or shims passing through the anterior plate and extending into the vertebral body above or below the anterior plate to provide anchoring in the anterior region of the fusion cage.

In operation, the present system comprises a method of positioning a spinal cage in an intervertebral space, by: (a) placing a C-shaped posterior body onto the distal end of an inserter; (b) positioning the C-shaped posterior body in the intervertebral space; (c) extending a plurality of shims through the inserter or directly into the C-shaped cage and through tracts in the C-shaped cage to guide the shims into the posterior vertebral body above and below the C-shaped posterior cage; (d) placing bone graft material into an open center region of the C-shaped posterior body; (e) attaching an anterior plate onto opposite ends of the C-shaped posterior body; and (f) extending a plurality of screws or shims through the anterior plate and into the vertebral body above and below the cage and plate.

The shims that pass through the C-shaped cage anchor the vertebral body to the C-shaped cage. Similarly, the screws or the shims that are placed through the anterior plate anchor the vertebral body above and below to the spinal cage.

An advantage of the present system is that it first secures the cage to the middle column/posterior vertebral body and then secures the anterior column/anterior vertebral body to the front end of the cage into place. Using the attached inserter or placing the shims directly through the cage, the surgeon is able to secure the posterior end of the spinal cage into place prior to inserting bone graft material into the open center space in the case. By providing both posterior and anterior fixation, a very sturdy spinal fusion cage system is provided. Specifically, by adding fixation in the posterior disc space in addition to the anterior fixation, the center of rotation is locked into the center of the construct. This balanced fixation advantageously results in improved fusion rates and less bracing needs as well as expanded indications for stand-alone fixation.

Advantageously as well, the surgeon enters the front of the spine, thereby reducing risk to the spinal column and accompanying nerves.

The present system includes several different embodiments that would all achieve the same advantageous fixation in the posterior aspect of the spinal fusion cage. These various embodiments provide for insertion of the shims through the lateral arms of the cage. Another embodiment has a central arm through which the shims are inserted. In preferred optional methods, these various embodiments of the present system can be used for contralateral fixation when using a lateral approach. As such, it is to be understood that the various embodiments of the present system can be used in both anterior and lateral surgical approaches.

DETAILED DESCRIPTION OF THE DRAWINGS

Figure 1A:
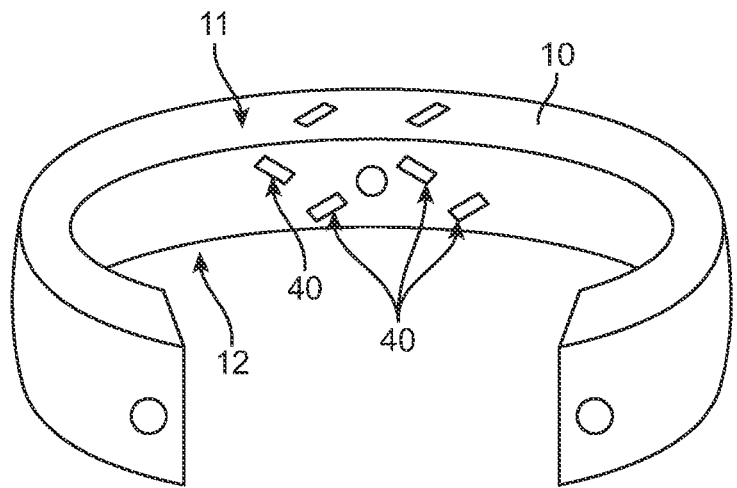
FIG. 1A is a front view of the C-shaped posterior body.
Figure 1B:
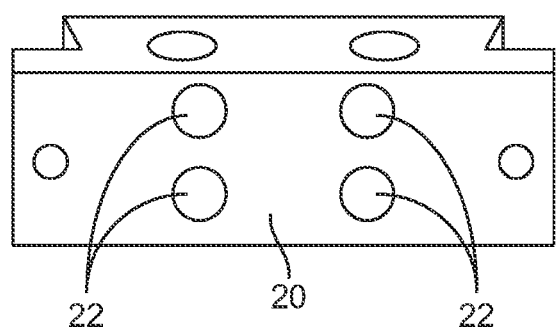
FIG. 1B is a front view of the anterior plate.

As seen in the accompanying figures, the present spinal cage comprises of two main components, the C-shaped posterior body 10 (FIG. 1A) and the anterior plate 20 (FIG. 1B). In preferred embodiments, the C-shaped posterior body has a curvilinear superior (top) surface 11 and inferior (bottom) surface 12 to allow better contact with vertebral endplates.

Figure 2A:
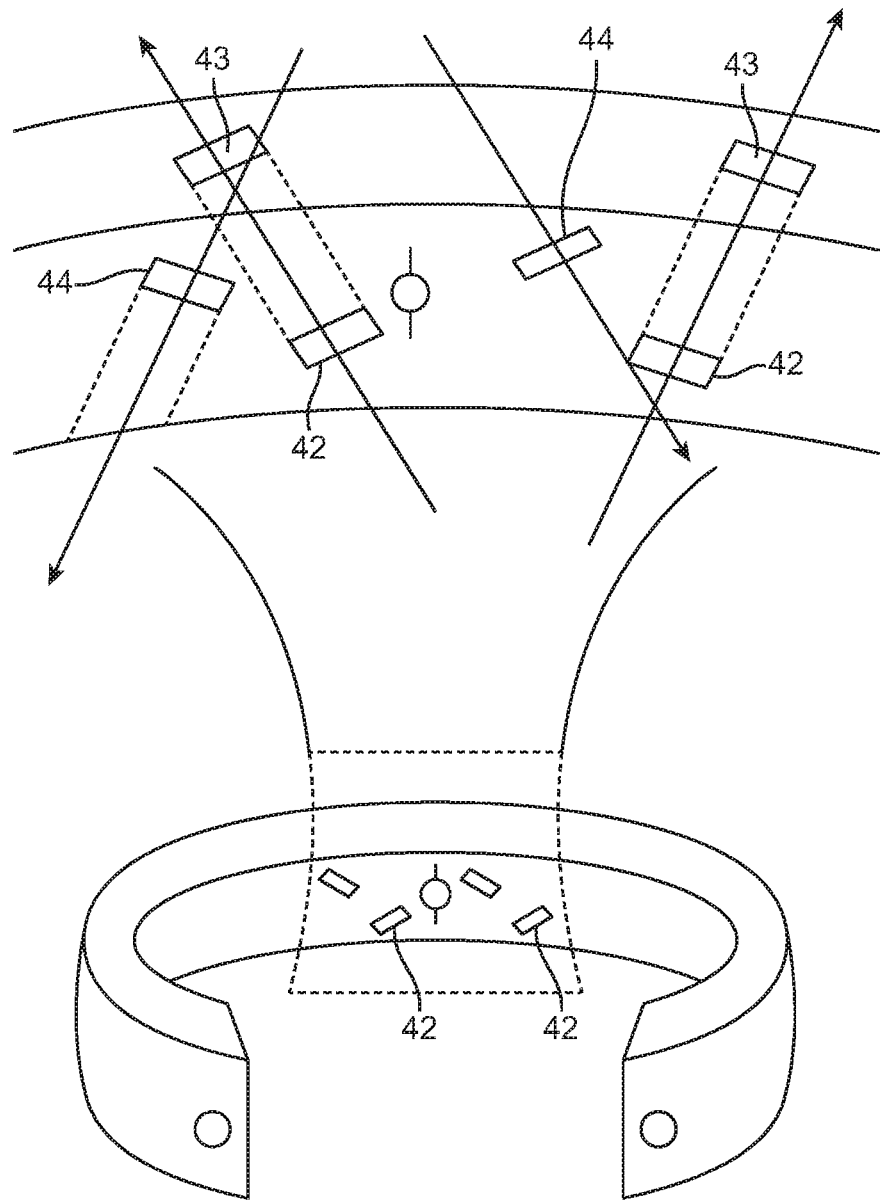
FIG. 2A is a perspective illustration of tracts passing through the C-shaped posterior body for the receipt of anchoring shims therethrough.
Figure 2B:
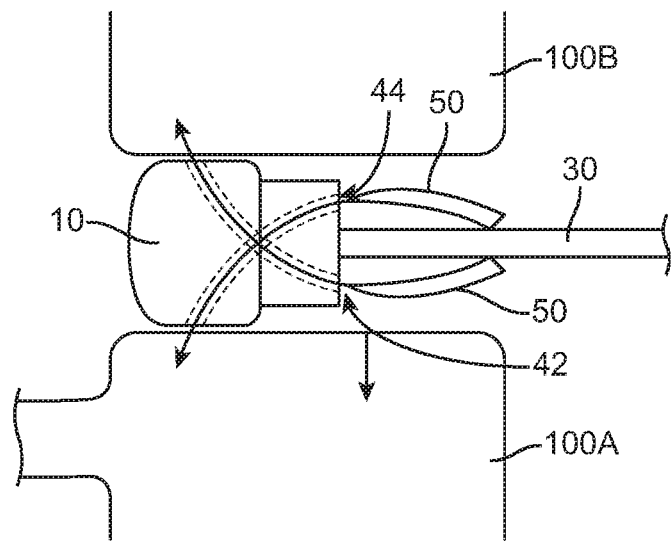
FIG. 2B is a side elevation view corresponding to FIG. 2A, prior to the insertion of the shims.
Figure 2C:
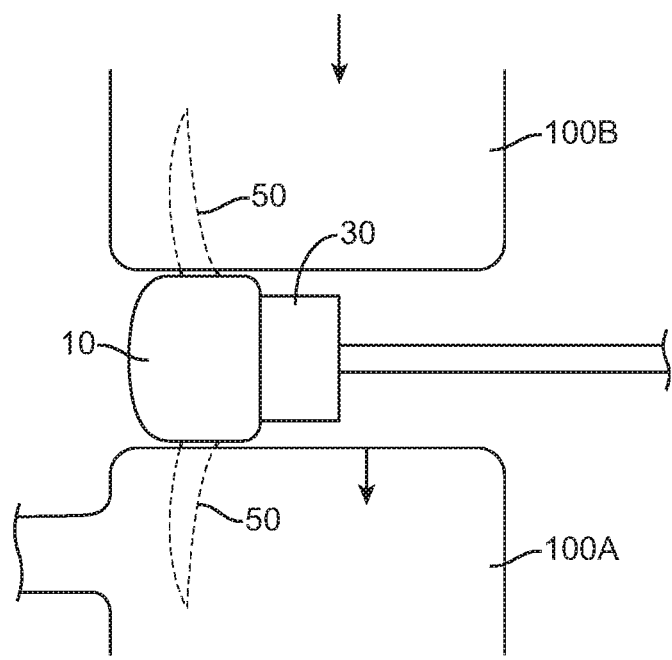
FIG. 2C is a side elevation view corresponding to FIG. 2A, after the insertion of the shims through the C-shaped posterior body.

As seen in FIG. 2A, there are tracts 40 in C-shaped posterior body 10. Tracts 40 are openings/passages through C-shaped posterior body 10 into which fixation shims 50 (FIGS. 2B and 2B) are inserted. When inserted, shims 50 pass through the tracts 40 in posterior body 10 and anchor into the posterior aspect of the superior and inferior vertebral bodies 100A and 100B of FIGS. 2B and 2C. These shims 50 anchoring into vertebral bodies 100A and 100B allows angle-stable fixation for the shims. FIG. 2A shows an optional preferred embodiment with tracts (passageways) 42 permitting a shim 50 to emerge upwardly out of top openings 43 and into vertebral body 100B. Similarly, tracts (passageways 44) permitting a shim 50 to emerge downwardly out of bottom openings (not shown) and into vertebral body 100A. The number of tract would likely be 2 to 4 but it is to be understood that the present invention isn't limited to any particular number of tracts or shims. FIG. 2B illustrates the placement of posterior body 10 with an inserter 30 prior to inserting shims 50 into tracts 40 (i.e.: tracts 42 and 44 in FIG. 2A). Next, FIG. 2C illustrates shims 50 received through tracts 42 and 44, passing into vertebral bodies 100A and 100B. As seen in FIGS. 2B and 2C, posterior C-shaped body 10 may be attached to inserter 30 which is used both to guide the posterior body 10 into its final position within the disc space (i.e.: between vertebral bodies 100A and 100B) and also to guide the fixation shims 50 through posterior body 10.

Figure 3A:
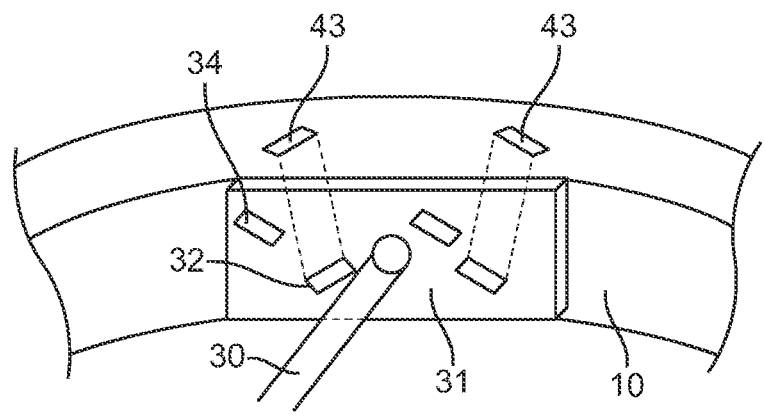
FIG. 3A is a perspective view of an inserter having holes passing therethrough that align with the shim tract holes in the C-shaped posterior body.
Figure 3B:
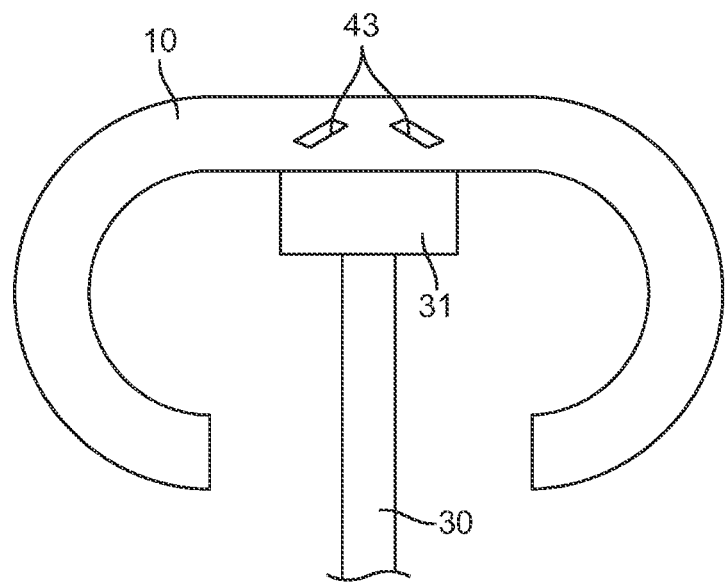
FIG. 3B is a top plan view corresponding to FIG. 3A.

As seen in FIGS. 3A and 3B, inserter 30 may optionally consist of a guide portion 31 that attaches to the C-shaped body 10 that will then align the tracks 32 with the tracts 43 in posterior body 10.

Figure 4A:
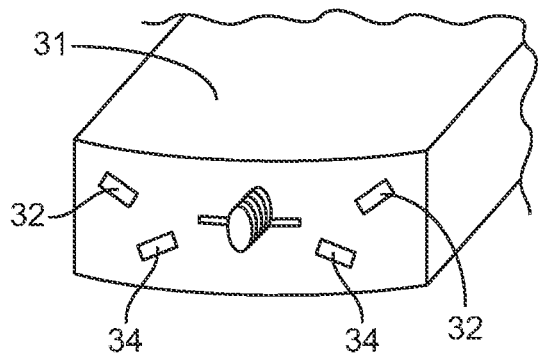
FIG. 4A is an illustration of the posterior face of the inserter showing the holes passing therethrough that align with the shim tract holes in the C-shaped posterior body.
Figure 4B:
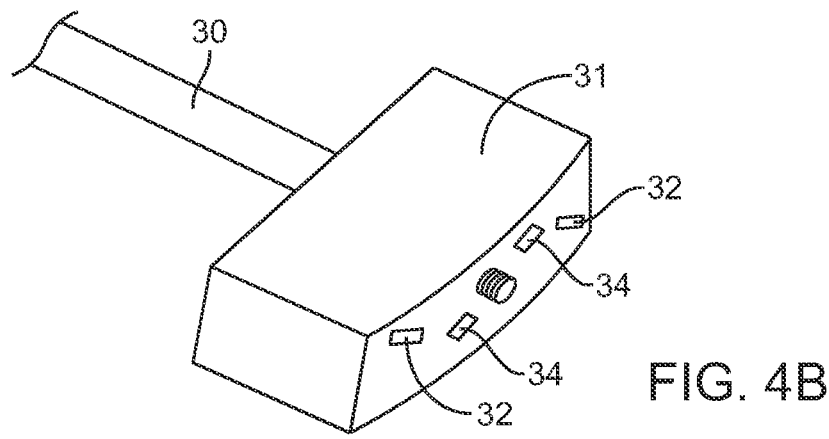
FIG. 4B is a top perspective view corresponding to FIG. 4A.
Figure 4C:
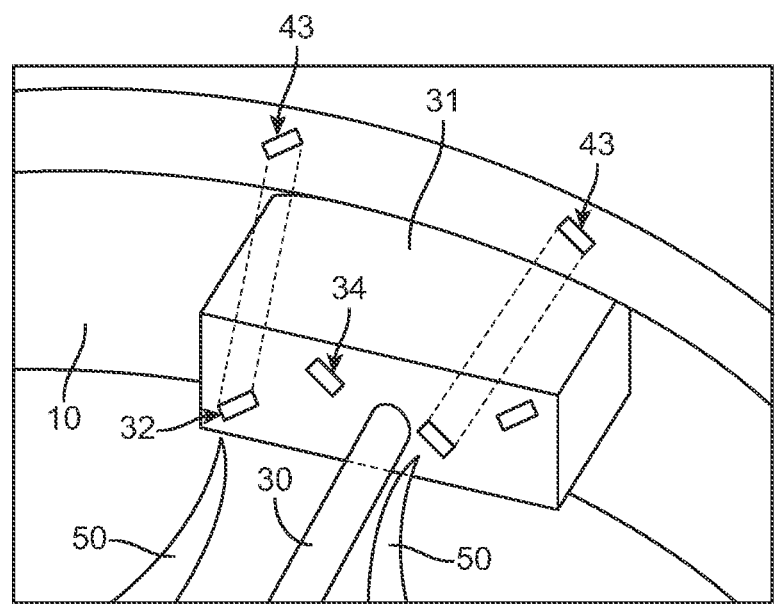
FIG. 4C is a front perspective view showing the placement of the inserter against the interior surface of the C-shaped posterior body.

As also seen in FIGS. 4A, 4B, and 4C, guide portion 31 of inserter 30 preferably has curved tracts 32 that aligns with tracts 43 in posterior body 10. Once inserter 30 is attached to posterior body 10 and posterior body 10 is in the intervertebral position, a shim 50 can then be inserted into guide portion 31 of inserter 30 and then tamped through C-shaped posterior body 10, with the distal end of the shim 50 then passing into the vertebral body (100A or 100B) using a flexible tamp. Alternatively, shims 50 can be placed within inserter 30 before posterior body 10 is positioned within the disc space to allow for a smoother insertion of the shims.

Figure 5A:
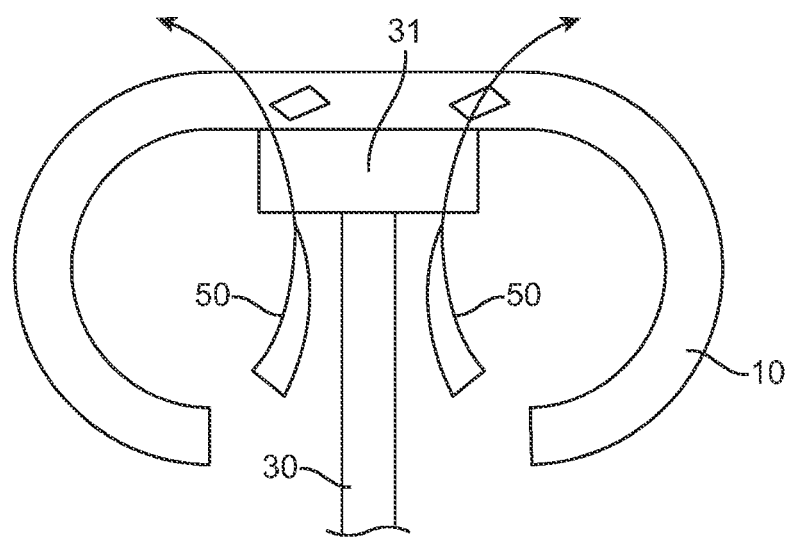
FIG. 5A is a top plan view showing the path of the shims through the inserter and C-shaped posterior body.
Figure 5B:
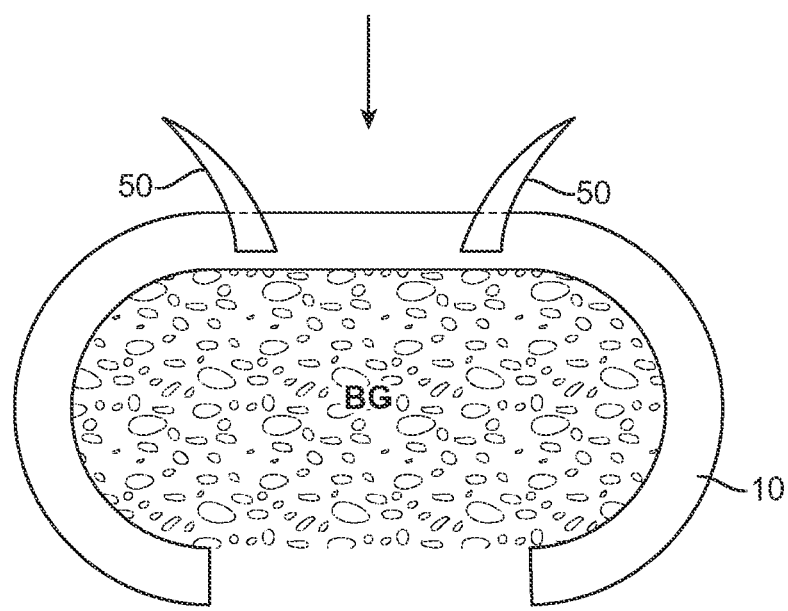
FIG. 5B shows the shims inserted into the adjacent vertebrae, with bone graft material packed into the center of the C-shaped posterior body.
Figure 5C:
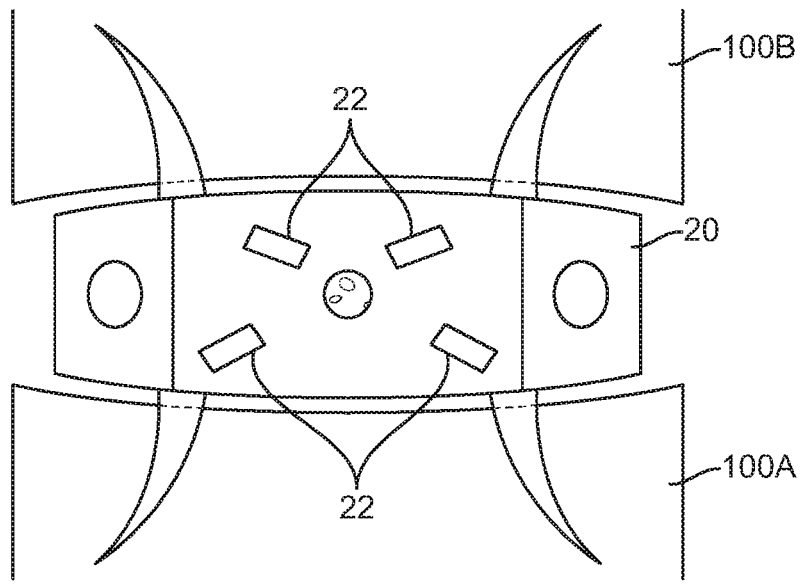
FIG. 5C is a front elevation view corresponding to FIG. 5A.
Figure 5D:
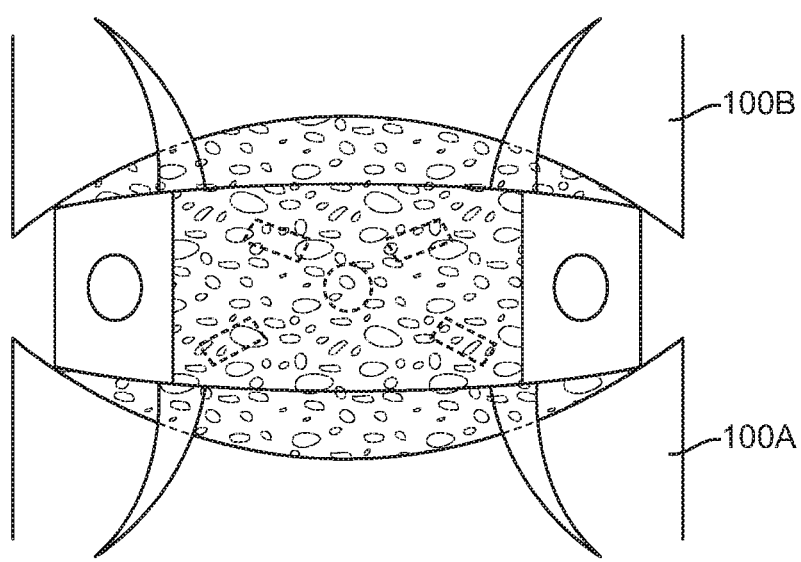
FIG. 5D is a front elevation view corresponding to FIG. 5B.

Once posterior fixation is completed (as seen in FIG. 5A), the inserter 30 is removed and bone graft material BG can be packed into the cage (in the open area formed within the curved shape of the posterior body 10 as seen in FIG. 5B). Packing the bone graft after cage placement rather than before offers the advantage of a more uniform contact of the bone graft with the anterior endplate 20. If the spinal cage was instead first packed with bone graft material prior to insertion into the intervertebral space, then the bone graft material BG would only make contact with the vertebral bodies 100A and 100B if the cage perfectly fits the contours of the disc space, which can be very difficult to do. FIG. 5C illustrates such a "lucky" placement where the contours of the spinal cage (formed by posterior portion 10 and anterior portion 20) ideally match the shapes of vertebral bodies 100A and 100B. In contrast, FIG. 5D illustrates the situation where the contours of the spinal cage do not exactly match the shapes of vertebral bodies 100A and 100B, but since the bone graft material BG was instead packed after placement of the spinal cage, the bone graft material BG fills any voids that remain, even if the cage does not fit perfectly. (Note, the position of bone graft material BG is shown as a cut away view, with the bone graft material filling the full spaces between the opposing vertebrae). Once the bone graft material has been packed in the space formed by curved C-shaped posterior body 10, the anterior plate 20 is then attached. Anterior plate 20 will preferably have a screw on both its left and right sides that will be used to mate with the C-shaped posterior body 10 of the spinal cage. Preferably, anterior plate 20 will have 4 screw holes 22 through which traditional placement of the screws can be done to stabilize the anterior part of the construct with fixation into the bone.

In preferred aspects, placement of the shims/blades would be performed through a fixed angle guide 32 attached to the posterior aspect of the cage (for example, as seen in FIGS. 3A and 4C). This guide 32 guides shims 50 blades in a predetermined trajectory, allowing for safe and reliable placement of the present devices without introducing human error. Guide 32 could optionally consist of four chambers with curved interior surfaces (and openings 32 and 34) that would direct shims 50 through posterior body 10 and into vertebral bodies 100A and 100B. The preferred angle of entry into the vertebra to achieve the most stable angle of fixation would be somewhere between 30 to 45 degrees from horizontal (however, the present invention is not limited to these particular angles).

In preferred aspects, a staggered entry into the spinal cage would allow for the strongest fixation of the shims 50 within the spinal cage while at the same time maximizing the amount of the shim 50 that is able to enter the vertebral body 100A or 100B. The inserter 30 could preferably thread into the cage to allow easy placement of the cage into the disc space and insertion of the posterior fixation without having to change any of the instrumentation.

Shims/blades 50 could optionally be designed in a variety of ways. They are preferably curved in order to allow for placement within the confines of the disc space. They could optionally be flat with serrated edges, diamond shaped, twisting, U- or V-shaped, T-shaped, etc. Once seated into the posterior body 10, shims 50 will lock into place so that they do not back out.

The preferred "open face" (i.e. C-shaped) design of posterior body 10 would provide ready access to the posterior aspect of the cage. Once the posterior instrumentation is inserted, bone graft material can be packed into the cage and the anterior plate 20 can be placed to close the medullary canal of the cage.

Figure 6A:
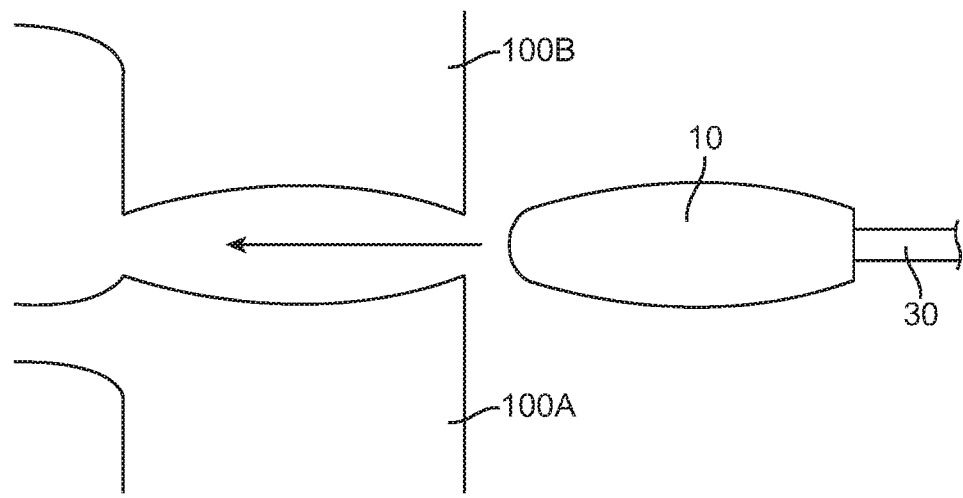
FIG. 6A is a first step in the preferred method showing the C-shaped posterior body about to be inserted into the intervertebral space with an inserter.
Figure 6B:
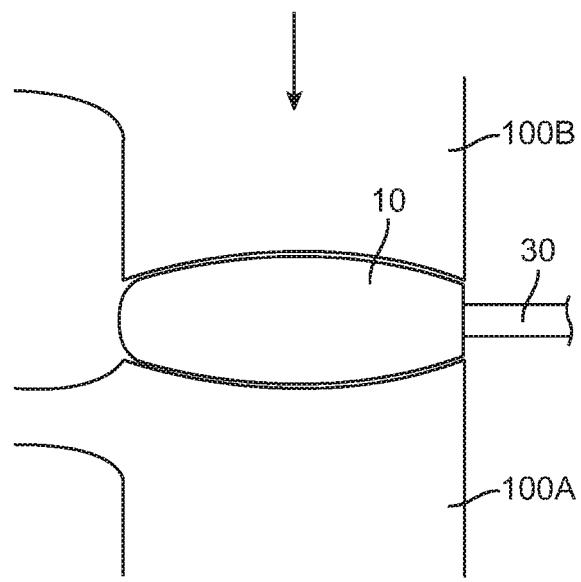
FIG. 6B is a second step in the preferred method with the C-shaped posterior body placed into its final position between the vertebrae.
Figure 6C:
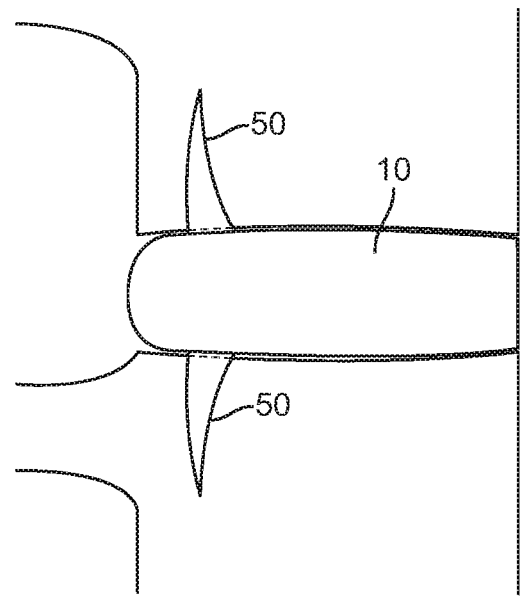
FIG. 6C is a third step in the preferred method with the shims deployed, thereby anchoring the posterior end of the C-shaped posterior body into the adjacent vertebrae above and below the C-shaped posterior body.
Figure 6D:
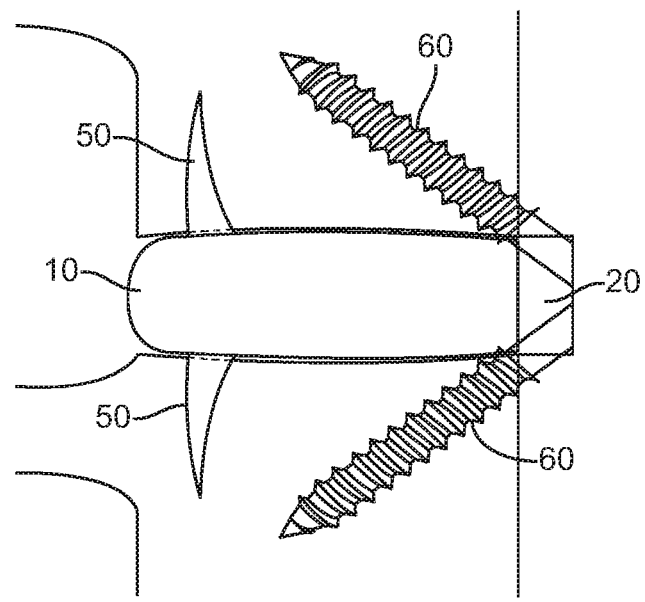
FIG. 6D is a fourth step in the preferred method with screws passing through the anterior plate, thereby: (a) locking the anterior plate onto the C-shaped posterior body (and thereby sealing the bone graft material within the interior of the C-shaped posterior body); and (b) anchoring the anterior end of the spinal cage into the adjacent vertebrae above and below the anterior plate.

FIG. 6A is a first step in the preferred method showing the C-shaped posterior body 10 about to be inserted into the intervertebral space with an inserter 30. FIG. 6B is a second step in the preferred method with the C-shaped posterior body 10 placed into its final position between the vertebrae 100A and 100B. FIG. 6C is a third step in the preferred method with shims 50 deployed, thereby anchoring the posterior end of the C-shaped posterior body 10 into the adjacent vertebrae above and below the C-shaped posterior body. Lastly, FIG. 6D is a fourth step in the preferred method with screws 60 passing through the anterior plate 20, thereby: (a) locking the anterior plate 20 onto the C-shaped posterior body 10 (and thereby sealing the bone graft material within the interior of the C-shaped posterior body); and (b) anchoring the anterior end of the spinal cage into the adjacent vertebrae above and below the anterior plate.

In further optional embodiments, the spinal cage may have a T-shaped posterior cage portion that would be placed first and mated with another T-shaped plate anteriorly after bone graft placement. This would then form a curvilinear H-shaped cage with open sides that would allow for a larger amount of bone graft placement as well as a better fit into the concave endplate and more modularity to increase the footprint and lordotic options available to users. Anterior fixation would be added after the construct assembly and bone graft placement is complete. When placed through the lateral approach, the cage is preferably modified to allow fixation to the contralateral aspect of the disc space. However, the general idea of an open cage with a combination cage insertion handle and shim inserter would remain the same.

One benefit of packing the bone graft material BG after placement of posterior body 10 is that the contact of the graft material would have better contact with the contours of the disc space. In contrast, spinal cages that are packed with bone graft material BG before placement into the disc space may lack consistent endplate/bone graft contact if the cage does not fit perfectly into the contour of the disc space. With the present design, the bone graft would fill the void fully and allow solid packing of the bone with near complete endplate/bone graft contact.

An advantage of the present system of adding anterior fixation (with screws 60) and posterior fixation (with shims 50) is that a more mechanically sound spinal fusion cage device is provided. Moreover, the present cage design resists both flexion and extension equally. In contrast, current designs are not able to stabilize against extension quite well. In addition, fixing only the anterior aspect of the vertebral bodies results in a hinge effect. Specifically, the posterior aspect of the disc space can open or distract to a greater extent than the native disc would have since only the anterior aspect of the vertebral bodies is fixed. When flexing, the vertebral bodies can lever on the anterior fixation, thereby resulting in this distraction. Fixing the posterior disc space would resist this distraction, thereby providing fixation that could possible rival the stability of traditional pedicle screw instrumentation, but without disrupting the posterior spinal anatomy.

Currently, the indications for stand-alone anterior fusion is limited to degenerative disc disease with no more than a grade 1 spondylolisthesis and no active instability. It is usually limited to 1 level surgery. Some would argue that any spondylolisthesis is a contraindication to stand-alone fixation and would recommend some sort of posterior fixation. This results in extra morbidity, increased risk of adjacent segment degeneration, blood loss, and infection. It also increases the cost of the surgery.

Spine surgery has moved away from isolated posterolateral fusion with pedicle screws alone because fixation at the posterior column alone is not strong enough to provide reliable results. Even though pedicle screws traverse all three columns of the spine, the axis of rotation is moved closer to the rod-screw interface. For this reason, most surgeons combine an interbody device with pedicle screws to support the anterior column to increase fusion rates and decrease failure of the screws. For the same reason, anterior fixation alone mechanically has the same limitations and moves the axis of rotation too far forward. Combining posterior column fixation with pedicle screws provides an extremely stable fixation but at the cost of the problems already listed. Providing fixation to the middle column with the present system would advantageously provide superior fixation and stability to either anterior or posterior fixation in isolation. In addition, this can be done with less morbidity than posterior fixation and also expand the indications for a stand-alone approach.

Figure 7A:
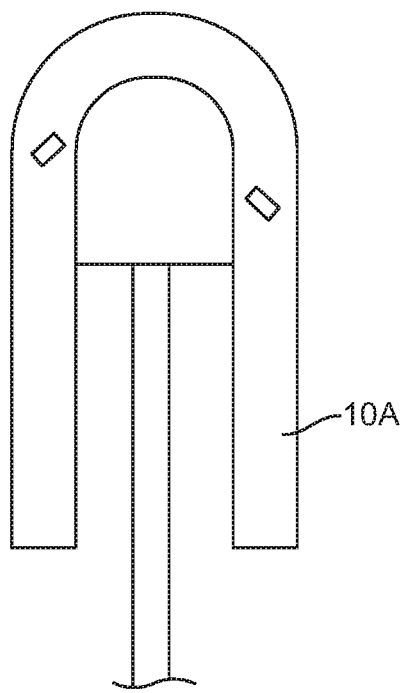
FIG. 7A is a top perspective view of an alternate embodiment, showing a laterally inserted spinal fusion cage design, and associated inserter.
Figure 7B:
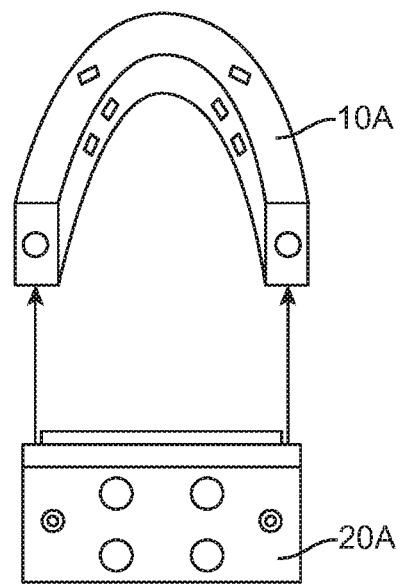
FIG. 7B is a front perspective view of the spinal fusion cage of FIG. 7A.
Figure 7C:
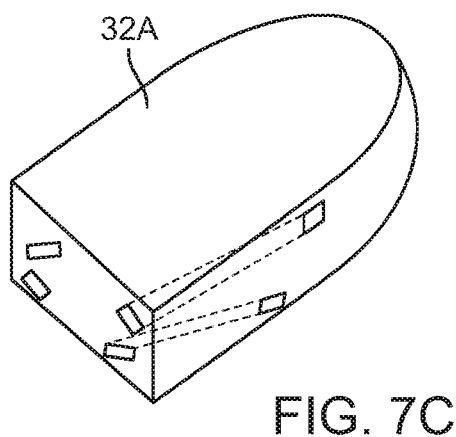
FIG. 7C is a perspective view of the distal end of the inserter.
Figure 7D:
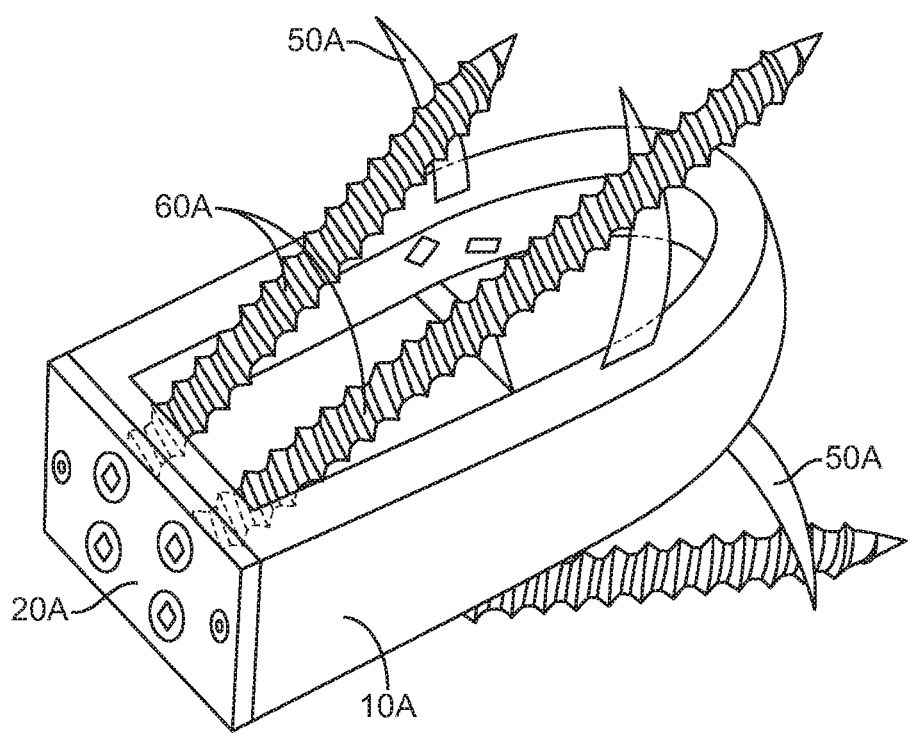
FIG. 7D is a perspective view of the assembled laterally inserted spinal fusion cage after it has been secured into position.

In optional embodiments illustrated in FIGS. 7A to 7D, a laterally inserted cage design is shown. This embodiment uses the same system of deployment and fixation as described above. Primarily, the difference between the lateral embodiment (FIG. 7A to 7D) and the anterior embodiment (FIG. 1A to 6D) is that the arms of the C-shaped body portion 10A are longer and straighter in the laterally-inserted design. FIG. 7C shows a perspective view of the distal end of inserter 30A, with the path of the shim tracts shown in dotted lines. The region where the shim passes through the C-shaped body portion 10A may be thicker (as compared to the anterior embodiment) in order to provide safe and accurate shim insertion. FIG. 7D is a perspective view of the assembled laterally inserted spinal fusion cage (10A and 20A) after it has been secured into position. The shims 50A (passing through the C-shaped body portion 10A) and the screws 60A (passing through the anterior portion 20A) can be clearly seen.

Figure 8A:
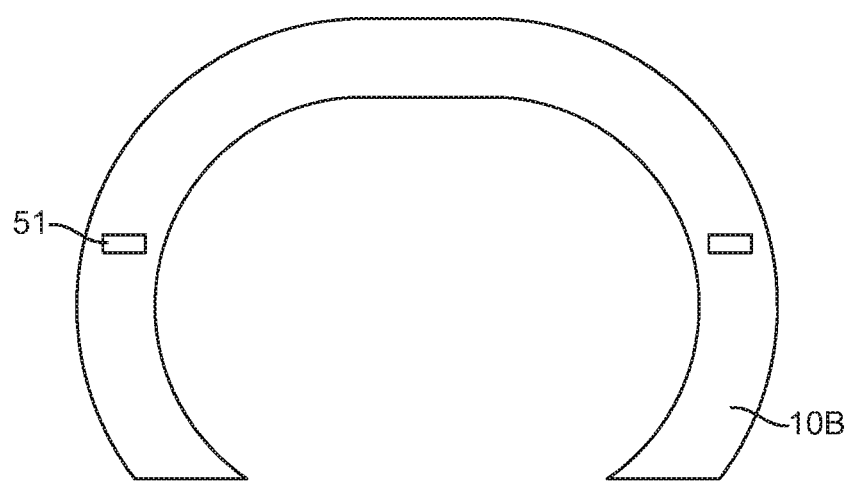
FIG. 8A is a top plan view of an alternate embodiment of a spinal fusion cage in which the shims pass through the lateral arms of the C-shaped posterior body.
Figure 8B:
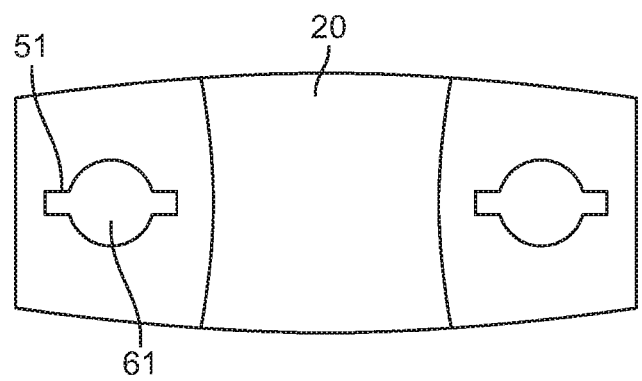
FIG. 8B is a front elevation view corresponding to FIG. 8A.
Figure 8C:
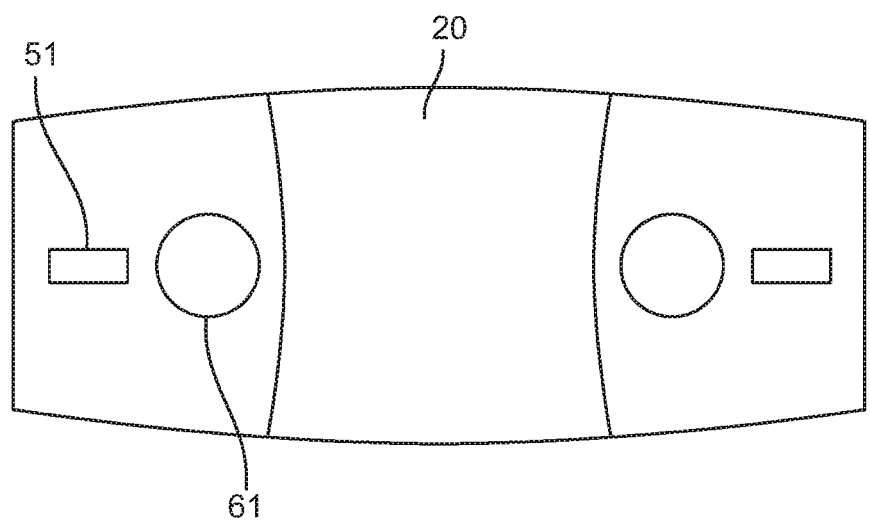
FIG. 8C is a front elevation view of the alternate embodiment corresponding to FIG. 8A.

In the optional embodiments of FIGS. 8A to 8C, the shims pass through the lateral arms of the C-shaped posterior body 10B. Alternatively, as seen in FIG. 8B, the shim insertion slot 51 can be in the anterior plate 20 and can pass through screw hole 61. Alternatively, as seen in FIG. 8C, the shim insertion slot 51 can again be in the anterior plate 20, but can be slightly spaced apart from the screw hole 61.

Figure 9A:
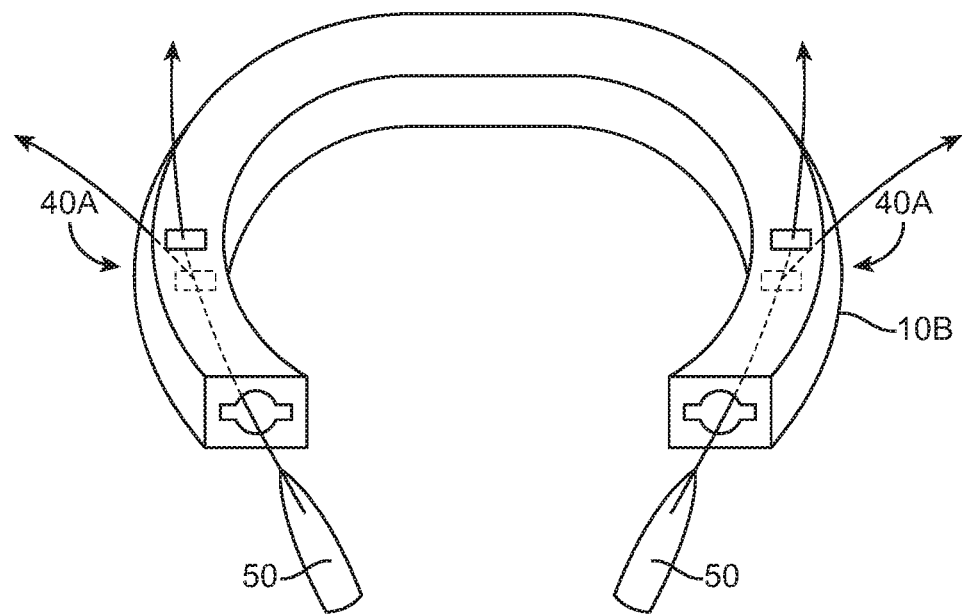
FIG. 9A is a front perspective view of an alternate embodiment of a spinal fusion cage having top and bottom shims passing through the lateral arms of the C-shaped posterior body.
Figure 9B:
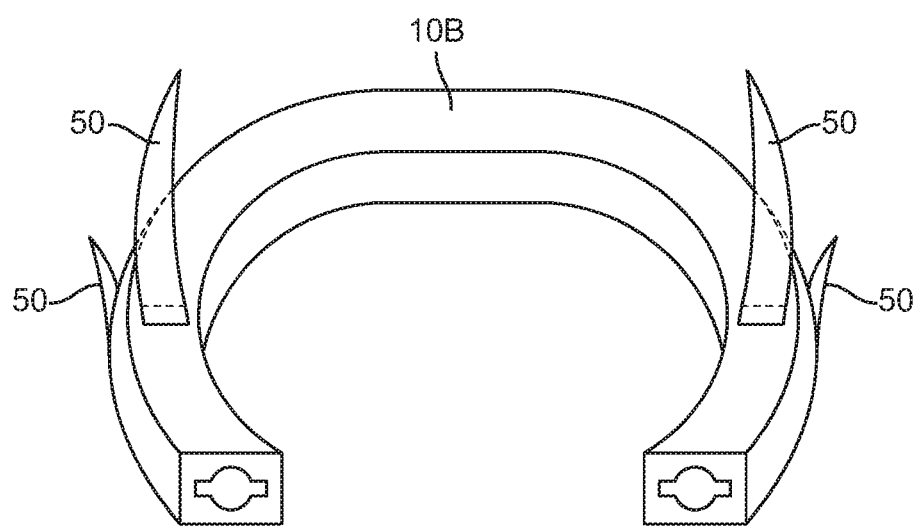
FIG. 9B is a front perspective view corresponding to FIG. 9A after the shims have been inserted.
Figure 9C:
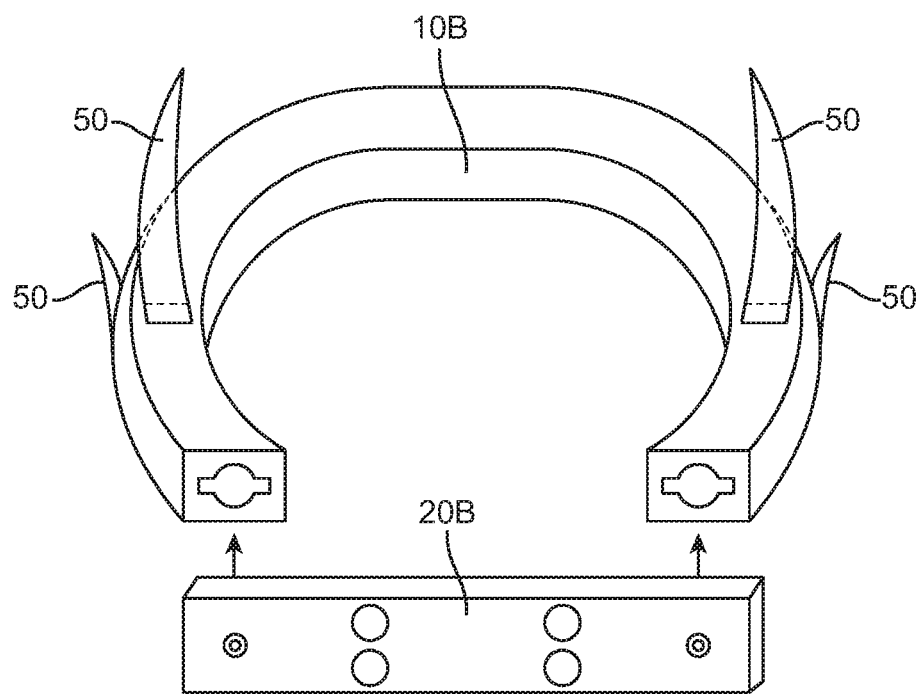
FIG. 9C is a front perspective view corresponding to FIG. 9B after the anterior plate has been attached.
Figure 9D:
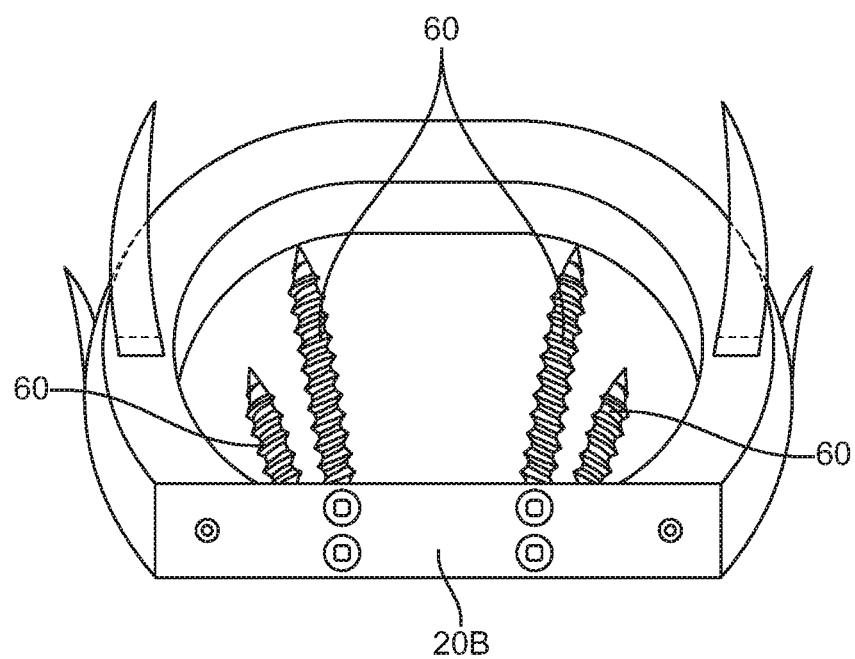
FIG. 9D is a is a front perspective view corresponding to FIG. 9C after the screws have been inserted.

As seen in FIGS. 9A to 9D, the shims can pass out through both the top and bottom of the holes 40A in the C-shaped posterior body. FIG. 9A shows the C-shaped posterior body prior to shim insertion. FIG. 9B shows the C-shaped posterior body 10B after shim insertion. FIG. 9C shows the anterior plate 20B being secured to posterior body 10B. Finally, FIG. 9D shows the screws 60 being inserted through the anterior plate 20B. The embodiments illustrated in FIGS. 8A to 9D could advantageously allow for more direct access to the entry site for placement of shims 50, which could possibly allow for placement of wider shims than through the posterior aspect of the spinal cage. The illustrated embodiments in FIGS. 8A to 9D would still allow for packing bone graft after placement of the cage which has the advantages that have already been set forth above.

Figure 10A:
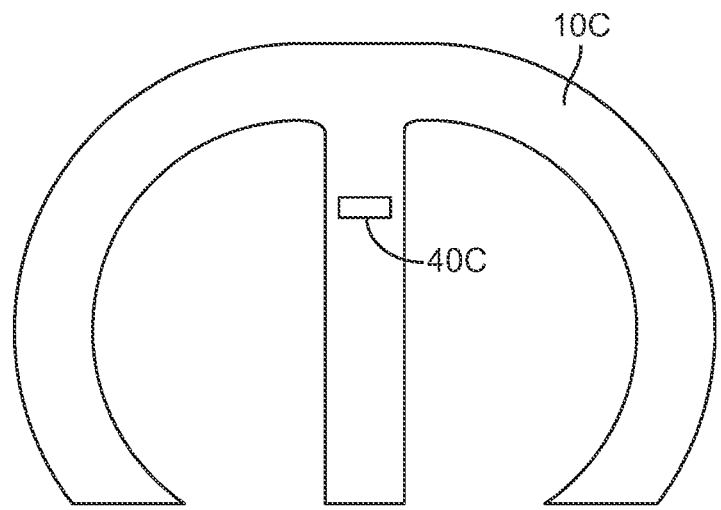
FIG. 10A is a top plan view of an alternate embodiment of a spinal fusion cage having an E-shaped posterior body.
Figure 10B:
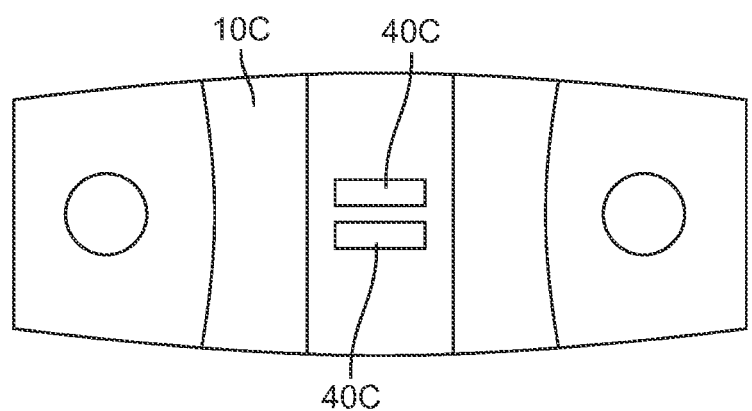
FIG. 10B is a front elevation view corresponding to FIG. 10A.

Lastly, FIGS. 10A and 10B show an alternate embodiment having an E-shaped posterior body 10C with shim holes 40C passing through holes 40C in the center of the E-shaped posterior body. A possible advantage of this embodiment is that it could provide more anterior access to the insertion sites of the shims.

What is claimed:

1. A spinal fusion cage, comprising: a C-shaped posterior body having opposite lateral ends and an open center region; a plurality of shim tracts passing through the C-shaped posterior body; a plurality of shims, each shim passing through one of the shim tracts and extending out from the C-shaped posterior body and configured for insertion into a vertebral body above or below the C-shaped posterior body; an anterior plate, the anterior plate being attachable to the opposite ends of the C-shaped posterior body; a plurality of screws passing through the anterior plate and configured for extension into a vertebral body above or below the anterior plate; and an inserter to guide the C-shaped posterior body into position within a disc space, wherein the inserter has holes that align with the shim tracts in the C-shaped posterior body.

2. The spinal fusion case of claim 1, wherein the plurality of screws attach the anterior plate to the C-shaped posterior body.

3. The spinal fusion cage of claim 1, wherein the plurality of shim tracts is 2 to 4 shim tracts.

4. The spinal fusion cage of claim 1, wherein the anterior plate has a plurality of holes to receive the plurality of screws therein.

5. The spinal fusion cage of claim 1, wherein the C-shaped posterior body has curved top and bottom surfaces.

6. The spinal fusion cage of claim 1, wherein: the shims secure the spinal cage to the posterior side of the vertebral bodies, and the plurality of screws are configured to secure the spinal cage to the anterior side of the vertebral bodies.

7. A method of positioning a spinal cage in an intervertebral space, comprising:
   placing a C-shaped posterior body onto a distal end of an inserter;
   positioning the C-shaped posterior body in the intervertebral space with the inserter;
   extending a plurality of shims through the inserter and through tracts in the C-shaped posterior body and into a vertebral body above or below the C-shaped posterior body, wherein the inserter has holes that align with the shim tracts in the C-shaped posterior body;
   placing bone graft material into an open center region of the C-shaped posterior body;
   attaching an anterior plate onto opposite ends of the C-shaped posterior body; and
   extending a plurality of screws through the anterior plate and into the vertebral body above or below the anterior plate.

8. The method of claim 7, wherein:
   the shims secure the spinal cage to the posterior side of the vertebral bodies, and
   the screws secure the spinal cage to the anterior side of the vertebral bodies.

9. A spinal fusion cage, comprising: a spinal fusion body; a plurality of shim tracts passing through a posterior portion of the spinal fusion body; a plurality of shims, each shim passing through one of the shim tracts and extending out from the posterior portion of the spinal fusion body and configured for insertion into a vertebral body above or below the posterior portion of the spinal fusion body, thereby being configured to affix the posterior portion of the spinal fusion body into the vertebral body; a plurality of screws passing through an anterior portion of the spinal fusion cage and configured for extension into a vertebral body above or below the anterior portion of the spinal fusion body, thereby being configured to affix the anterior portion of the spinal fusion body into the vertebral body; and an inserter to guide the C-shaped posterior body into position within a disc space, wherein the inserter has holes that align with the shim tracts in the posterior portion of the spinal fusion body.

10. The spinal fusion cage of claim 9, wherein the plurality of shim tracts is 2 to 4 shim tracts.

11. The spinal fusion cage of claim 1, wherein the C-shaped posterior body has curved top and bottom surfaces.

* * * * *